United States Patent

Storz

[11] Patent Number: 5,817,128
[45] Date of Patent: *Oct. 6, 1998

[54] MEDICAL TONGS

[75] Inventor: Karl Storz, Tuttlingen, Germany

[73] Assignee: Karl Storz GmbH & Co., Tuttlingen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 513,939

[22] PCT Filed: Mar. 10, 1994

[86] PCT No.: PCT/DE94/00247

§ 371 Date: Oct. 6, 1995

§ 102(e) Date: Oct. 6, 1995

[87] PCT Pub. No.: WO94/20034

PCT Pub. Date: Sep. 15, 1994

[30] Foreign Application Priority Data

Mar. 10, 1993 [DE] Germany ............ 43 07 539.8

[51] Int. Cl.⁶ .................................................. A61B 17/28
[52] U.S. Cl. ............................ 606/205; 606/51; 606/52
[58] Field of Search ................................ 606/205, 170, 606/206, 207, 51, 52; 600/564, 565

[56] References Cited

U.S. PATENT DOCUMENTS

| 2,113,246 | 4/1938 | Wappler . | |
| 2,518,994 | 8/1950 | Miller | 606/205 |
| 4,258,716 | 3/1981 | Sutherland | 606/170 |
| 4,674,501 | 6/1987 | Greenberg . | |
| 4,944,093 | 7/1990 | Falk | 606/205 X |
| 5,308,358 | 5/1994 | Bond et al. | 606/205 |

FOREIGN PATENT DOCUMENTS

| 0484671 | 5/1992 | European Pat. Off. . |
| 3741879 | 6/1988 | Germany . |
| 8905099 | 8/1989 | Germany . |
| 8905099 | 9/1989 | Germany . |
| 9007356 | 5/1991 | Germany . |
| 9007356 | 6/1991 | Germany . |
| 9202132 | 4/1992 | Germany . |
| 9214059 | 1/1993 | Germany . |
| 9211812 | 7/1992 | WIPO . |

*Primary Examiner*—Michael H. Thaler
*Attorney, Agent, or Firm*—Donald D. Mon

[57] ABSTRACT

Disclosed are medical tongs, in particular, for use in endoscopic surgery, having

- a handpiece, provided with a stationary and a movable handle,
- an external tube, which is connected to the stationary handle, and
- inside the external tube a moveably guided draw-rod, which actuates at least one of the two tong elements of the tong jaws and which is connected to the movable handle.

The present invention is distinguished by a bayonet element, which can be inserted into a bayonet insert inside the external tube and to which at least one of the tong elements is joined, being borne at the distal end of the draw-rod in such a manner that it can be moved relative to the draw-rod, and by being able to connect the external tube having the inserted draw-rod to the handpiece via a connection element with the proximal end of the draw-rod locking into a spring catch in the movable handle.

12 Claims, 2 Drawing Sheets

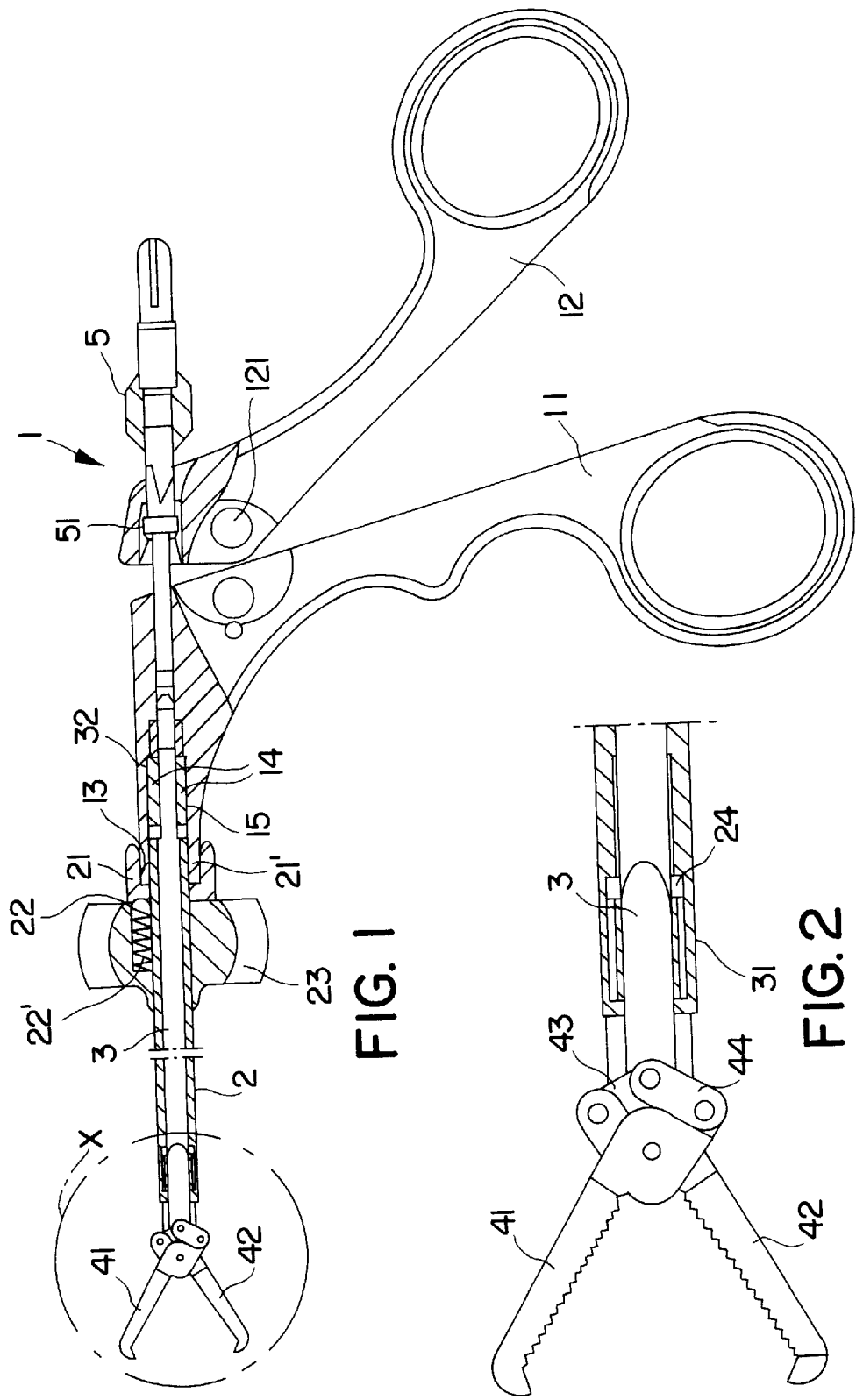

MEDICAL TONGS

TECHNICAL FIELD

The present invention relates to medical tongs, in particular, for use in endoscopic surgery according to the introductory part of claim 1.

Generic medical tongs, in particular, for use in endoscopic surgery are known from the document DE-U-90 07 356. These tongs are provided with a handpiece which has a stationary and a movable handle, a external tube which is connected to the stationary handle, and a draw element guided in a movable manner inside the external tube. This draw element operates at least one of the two tong elements of the jaws of the tongs and is connected to the movable handle.

STATE OF THE ART

The known generic tongs are provided with a handpiece having a stationary and a movable handle. Attached to the stationary handle is an external tube in which a draw-rod is guided in a movable manner which actuates at least one of the two elements of the tongs and is connected to the movable handle.

For a number of reasons, it would be desirable to be able to easily disassemble generic medical tongs, herein only cleaning and sterilization as well as the replacement of defect parts, respectively the upgrading, in particular, of the tong elements will be mentioned. State-of-the-art tongs, however, cannot be disassembled or only with difficulty. Moreover, it is difficult to reassemble disassembled tongs.

Providing medical tongs with a bayonet joint in order to be able to take them apart for cleaning and then easily reassemble them is known from the document DE-U-89 05 099, however these tongs are of another class than the one set forth in the introductory part of claim 1 of the present invention. However, the tongs known from this document have the drawback that the bayonet joint may unintentionally be released during insertion into the human body.

DESCRIPTION OF THE INVENTION

The object of the present invention is to improve medical tongs, in particular, for use in endoscopic surgery according to the introductory part of claim 1 in such a manner that it is easy to disassemble the tongs while at the same time ensuring proper function of the tongs following assembly without requiring additional measures.

A solution to this object according to the present invention is set forth in claim 1. Further improvements of the present invention are the subject matter of claims 2 to 14.

An element of the present invention is that a bayonet element which can be inserted into a bayonet insert inside the external tube and to which at least one of the elements of the tongs is joined is borne at the distal end of the draw-rod in such a manner that it can be moved relative to the draw-rod. The bayonet joint between the external tube and the draw-rod not only ensures easy removal of the draw-rod from the external tube, but the rotary position alignment prescribed by the bayonet action also ensures correct insertion of the draw-rod inside the external tube and secure attachment of the two elements to each other during assembly. The spring clamp element, engaging the draw-rod in a formfitting manner when the handpiece is attached, provided in the external tube ensures that the bayonet joint is not unintentionally released in the assembled state of the tongs.

In a further improvement of the present invention, the external tube containing the inserted draw-rod can be connected to the handpiece via a connection element, with the proximal end of the draw-rod locking into place in a spring catch in the movable handle of the handpiece. This embodiment ensures perfect connection to the handpiece, while retaining all the degrees of freedom, by way of illustration, for the rotation of the external tube containing the inserted draw-rod.

BRIEF DESCRIPTION OF THE DRAWING

The present invention is described by way of example in the following without the intention of limiting the scope and spirit of the present invention using a preferred embodiment with reference to the accompanying drawing to which is expressly referred with regard to the disclosure of all the invented details not made more apparent herein. Shown is in:

FIG. 1 a partial section of medical tongs,

FIG. 2 detail x from FIG. 1,

DESCRIPTION OF A PREFERRED EMBODIMENT

Figure 3:
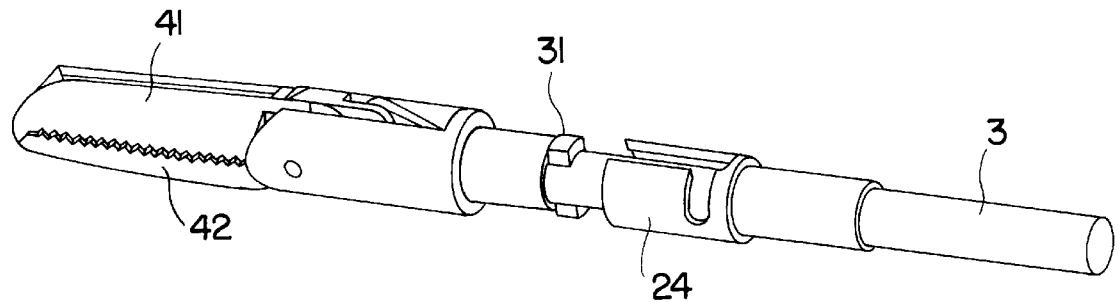
FIG. 3 the distal connection draw-rod/external tube.

FIG. 1 shows in a lateral view, respectively in a partial section medical tongs improved in accordance with the present invention, in particular, for use in endoscopic surgery. The tongs have a handpiece 1 with a stationary handle 11 and a movable handle 12. The movable handle 12 is joined in a pivotable manner to the stationary handle 11 via a joint 121, which is not illustrated in detail.

The stationary handle 11 is provided at the end facing the distal end of the tongs with a screw thread 13 (outer thread) onto which a screw element 21 with an inside thread 21' is screwed. The screw element 21 is connected in a rotatable manner to a handle element 23, which for its part is firmly connected to an external tube 2 of tongs 1.

In order to be able to set defined rotations, respectively rotation positions of the handle section 23, respectively of the external tube 2 relative to the screw element 21, respectively to the stationary handle 11, at least one ball 22 loaded by a spring 22' is provided, with this ball gripping respectively locking into place in the corresponding recesses in the screw element 21. The number of the rotation positions into which can be locked into place between the external tube 2 and the screw element 21 is prescribed by the number of recesses and their angles.

Naturally, other locking-in-place connections permitting a defined angle setting may be provided instead of a ball catch. Furthermore, a catch may be obviated so that a relative rotation position between the handle 11 and the external tube 2 is fixed, by way of illustration, by a friction connection.

Inside the external tube 2, a draw-rod is guided in such a movable manner that it follows the rotation of the external tube 2 relative to the stationary handle 11. This is explained in connection with FIGS. 2 and 3. Draw-rod 3 is connected to the movable handle 12. By moving draw-rod 3, tong elements 41 and 42 provided at the distal end of the tongs and forming the so-called tong jaws 4 are actuated, i.e. opened and closed, in the manner described below.

Furthermore, by means of the rotational movement tong elements 41 and 42 can be set relative to the handpiece 1 with regard to their rotational position according to the respective application.

FIG. 2 shows detail x from FIG. 1 to explain the actuation of the movable tong elements 41 and 42.

FIG. 3 shows a perspective representation of the bayonet joint between the draw-rod 3 and the external tube 2.

A bayonet element 31, which can be inserted into a bayonet insert 24 inside the external tube 2, is borne on the distal end of the draw-rod 3 in a such a manner that it can be moved relative to the draw-rod. The two tong elements 41 and 42 are joined to the bayonet element 31. The actuation of the two tong elements 41 and 42 occurs via pivotal elements 43 and 44 (FIG. 2). Due to the bayonet action between elements 31 and 24, the bayonet element 31 is fixed relative to the external tube in such a manner that a movement of the draw-rod 3 can actuate, i.e. open respectively close, the tong elements 41 and 42. At the same time, the draw-rod 3 follows a rotation of the external tube 2.

Naturally, all the other embodiments of the so-called tong jaws like those known from the state of the art are also possible. In particular, the tong jaws, i.e. the elements 41 and 42, can be designed in such a manner that one element is firmly connected to the bayonet element 31 and thus is not pivoted upon opening the tong jaws, while the other element is pivoted by a movement of the draw-rod.

Figure 4:
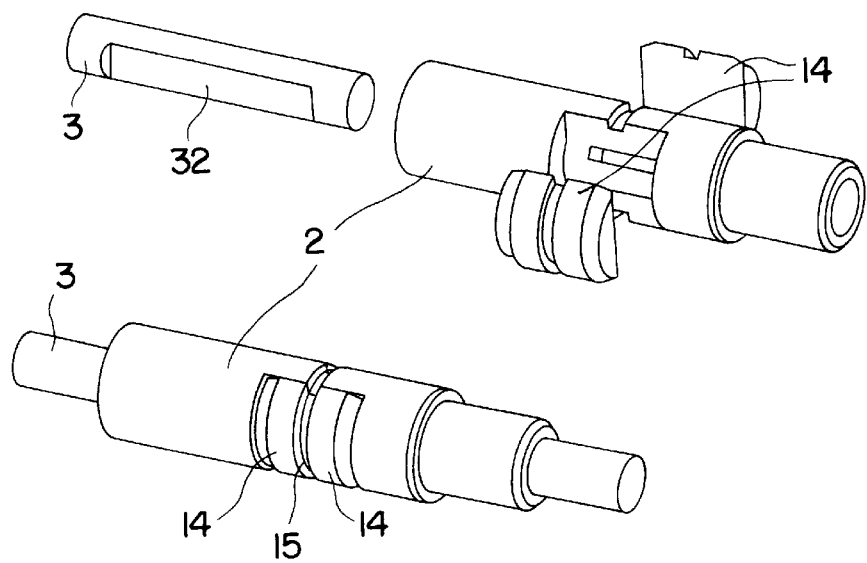
FIG. 4 the proximal connection draw-rod/external tube.

In order to prevent torsion of the comparatively thin draw-rod 3 during the relative rotation between external tube 2 and handpiece 1, the draw-rod 3 is borne at its proximal end in the manner made more apparent in FIG. 4.

As FIG. 4 shows draw-rod 3 is provided at its proximal end region with two flat sections 32 which face each other and by means of which it can be inserted into a clamp element 14 at the proximal end region of external tube 2. Reference No. 15 stands for the spring ring which prestresses the two halves of the clamp element 14 in the direction toward flat sections 32 of the draw-rod 3.

Furthermore, the proximal end of the draw-rod 3 is designed in such a manner that it locks into a spring catch 51 in the movable handle 12 of handpiece 1. For this purpose, the draw-rod 3 may be designed spherical in shape at its proximal end.

The catch 51 can be moved in the direction of the longitudinal axis of the draw-rod 3 by an actuating element 5 in such a manner that the opening of the tong jaws can be adjusted at a specific position of the movable handle 12 relative to the stationary handle 11.

In the preceding, the present invention has been described using a preferred embodiment, with many different modifications, of course, being possible.

By way of illustration, a not depicted spring may snap the movable handle 12 into a position in which the two tong elements 41 and 42 are closed.

Furthermore, the two handles 11 and 12 may be fixed relative to each other by a state of the art saw-tooth type catch.

In another advantageous embodiment, the external tube is composed of a metallic internal tube and a jacket tube made of an insulating material. This embodiment of the tongs may, by way of illustration, be utilized as a HF resectoscope. It is especially advantageous if the jacket tube made of an insulating material is connected to the actual tongs via a bayonet joint.

The end of the metal shaft close to the patient is protected against current damage in the urethra by means of an endpiece made of an insulating material. The endpiece is often damaged by sparks occurring when high-frequency currents are employed. The endpiece is, therefore, susceptible to damage and is nuisance in practice.

In another further embodiment of the subject matter of the present invention, the shaft of the resectoscope is composed of two separable parts, noteably the internal metallic part and the external part made of a non-conductive material. The external part is connected to the tongs by means of a lock, respectively a bayonet joint.

Preferably, the end which is close to the patient and is made of a non-conductive material extends several millimeters over the metallic part so that no high-frequency-current damage occurs. The inexpensive part made of non-conductive material can be disposable, but it may also be a reusable part, which by way of illustration can be autoclaved.

In any case, the invented design permits easy cleaning and/or replacement of parts as well as "reassembly" of the tongs without any danger of malfunction.

What is claimed is:

1. Medical tongs, in particular, for use in endoscopic surgery, having:

a pair of tong elements (41,42);

a handpiece (1), provided with a stationary and a movable handle (11,12);

an external tube (2), which is connected to said stationary handle (11); and inside said external tube (2) a movable guided draw-rod (3), which actuates at least one of said two tong elements (41,42) which is connected to said movable handle (12), characterized by a bayonet element (31), which can be inserted into a bayonet insert (24) inside said external tube (2) and to which at least one of said tong elements (4, 42) is joined, being borne on the distal end of said draw-rod (3) in such a manner that it can be moved relative to said draw-rod, and further characterized in said external tube (2) a spring clamp element (14,15) is provided which engages said draw-rod (3) in a formfitting manner when said handpiece is attached, said spring clamp element comprising a flat region on said draw-rod, a pair of clamp elements adapted to engage said flat region and a flat portion of said external tube to hold the draw-rod and external tube against relative rotation while permitting their axial relative movement, and an encircling spring holding the clamp elements against the draw tube, while being fitted in said fixed handle.

2. Tongs according to claim 1, characterized by being able to connect said external tube (2) having said inserted draw-rod (3) to said handpiece (1) via a connection element (13,21), with the proximal end of said draw-rod (3) locking into a catch (51) in said movable handle (12) of said handpiece (1).

3. Tongs according to claim 2, characterized by being able to move said catch (51) on said movable handle (12) by means of an actuating element (5) in such a manner that the opening of the tong jaws (4) can be set.

4. Tongs according claim 2, characterized by the connection element which connects said external tube (2) to the handpiece (1) being a screw element (13, 21).

5. Tongs according to claim 2, characterized by said external tube (2) being rotatable relative to a part (21) of said connection element attached to said handpiece (1).

6. Tongs according to claim 5, characterized by being able to set defined rotational positions between said external tube (2) and said handpiece (1).

7. Tongs according to claim 6, characterized by a ball/catch connection defining said rotational positions.

8. Tongs according to claim 1, characterized by said draw-rod (3) having at its proximal end section two flat sections (32) which face each other and into which said spring clamp element (14, 15) of said external tube (2) engages in a formfitting manner.

9. Tongs according to claim 1, characterized by both said tong elements (41, 42) being movable.

10. Tongs according to claim 9, characterized by said tong elements (41, 42) being connected to said draw-rod via pivotal elements (43, 44).

11. Tongs according to claim 1, characterized by said external tube (2) being composed of a metallic internal tube and a jacket tube made of an insulating material.

12. Tongs according to claim 11, characterized by said jacket tube made of an insulating material being connected to the actual tongs via a bayonet joint.

* * * * *